(12) United States Patent
Jackson et al.

(10) Patent No.: US 11,497,581 B2
(45) Date of Patent: Nov. 15, 2022

(54) ENDOSCOPE CLEANING AND INSPECTION SYSTEM AND METHOD

(71) Applicant: Medivators Inc., Minneapolis, MN (US)

(72) Inventors: Mark Jackson, Great Wakering (GB); Joshua J. Korth, St. Louis Park, MN (US)

(73) Assignee: Medivators Inc., Minneapolis, MN (US)

( * ) Notice: Subject to any disclaimer, the term of this patent is extended or adjusted under 35 U.S.C. 154(b) by 0 days.

(21) Appl. No.: 17/289,502

(22) PCT Filed: Nov. 1, 2019

(86) PCT No.: PCT/US2019/059355
§ 371 (c)(1),
(2) Date: Apr. 28, 2021

(87) PCT Pub. No.: WO2020/096888
PCT Pub. Date: May 14, 2020

(65) Prior Publication Data
US 2021/0386508 A1 Dec. 16, 2021

Related U.S. Application Data

(60) Provisional application No. 62/755,829, filed on Nov. 5, 2018.

(51) Int. Cl.
*A61B 90/70* (2016.01)
*B08B 9/032* (2006.01)
(Continued)

(52) U.S. Cl.
CPC .............. *A61B 90/70* (2016.02); *B08B 9/032* (2013.01); *G01M 3/2815* (2013.01); *G01M 3/38* (2013.01);
(Continued)

(58) Field of Classification Search
None
See application file for complete search history.

(56) References Cited

U.S. PATENT DOCUMENTS 6,013,034 A   1/2000   Fernandes Da Cunha Vaz et al.
6,174,291 B1  1/2001   McMahon et al.
(Continued)

FOREIGN PATENT DOCUMENTS

CN   1613308   5/2005
CN   1836508   9/2006
(Continued)

OTHER PUBLICATIONS

International Search Report and Written Opinion of the International Searching Authority dated Feb. 10, 2020, of International PCT Application No. PCT/US2019/59364 filed Nov. 1, 2019.
(Continued)

*Primary Examiner* — Hung Q Dang

(57) ABSTRACT

Embodiments of a system and method for endoscope cleaning and inspection are disclosed. In an example, an endoscope cleaning and inspection unit includes cleaning and testing capabilities operated via control equipment and a display screen, to operate leak testing equipment, flush control equipment, and optical inspection equipment for leak testing, flushing, rinsing, and inspection of an endoscope interior chamber (lumen) and exterior surfaces. In a further example, the endoscope cleaning and inspection unit may further operate and receive information from a borescope imaging device or a magnification imaging device, using an imaging sensor to capture images of an endoscope lumen or surface respectively, as captured or output on the display screen. Further embodiments provide for control,
(Continued)

monitoring, data collection, data input, and data output with such imaging devices via the endoscope cleaning and inspection unit.

15 Claims, 7 Drawing Sheets

(51) Int. Cl.

| | | |
|---|---|---|
| *G01M 3/28* | (2006.01) | |
| *G01M 3/38* | (2006.01) | |
| *G01N 21/88* | (2006.01) | |
| *G01N 21/954* | (2006.01) | |
| *G06F 3/0488* | (2022.01) | |
| *H04N 5/232* | (2006.01) | |
| *H04N 7/18* | (2006.01) | |
| *H04N 5/225* | (2006.01) | |

(52) U.S. Cl.
CPC ....... *G01N 21/8851* (2013.01); *G01N 21/954* (2013.01); *G06F 3/0488* (2013.01); *H04N 5/23203* (2013.01); *H04N 5/23296* (2013.01); *H04N 7/183* (2013.01); *A61B 2090/701* (2016.02); *A61B 2090/702* (2016.02); *B08B 2209/032* (2013.01); *H04N 2005/2255* (2013.01)

(56) References Cited

U.S. PATENT DOCUMENTS

| | | |
|---|---|---|
| 6,694,176 B1 | 2/2004 | Tsujita et al. |
| 6,793,880 B2 | 9/2004 | Kippenhan, Jr. |
| 7,905,831 B2 | 3/2011 | Noguchi et al. |
| 7,918,788 B2 | 4/2011 | Lin et al. |
| 7,942,810 B2 | 5/2011 | Uchimura et al. |
| 8,084,756 B2 | 12/2011 | Tokhtuev et al. |
| 8,227,766 B2 | 7/2012 | Chapman |
| 8,353,818 B1 | 1/2013 | Sasaki |
| 8,454,937 B2 | 6/2013 | Claudio |
| 8,593,626 B2 | 11/2013 | Brouwer |
| 8,933,008 B2 | 1/2015 | Whiteley et al. |
| 9,167,160 B2 | 10/2015 | King |
| 9,566,415 B2 | 2/2017 | Soutorine |
| 9,649,019 B2 | 5/2017 | Noack |
| 9,820,630 B2 | 11/2017 | Tomita |
| 9,892,513 B2 | 2/2018 | Gurevich et al. |
| 9,907,624 B2 | 3/2018 | Vazales et al. |
| 10,254,224 B2 | 4/2019 | Bolduc et al. |
| 10,266,793 B2 | 4/2019 | Labib et al. |
| 10,358,622 B2 | 7/2019 | Stokes et al. |
| 10,660,505 B2 | 5/2020 | Irion et al. |
| 10,702,353 B2 | 7/2020 | Tesar |
| 10,702,619 B2 | 7/2020 | Fang et al. |
| 10,705,020 B2 | 7/2020 | Baribeau |
| 10,709,313 B2 | 7/2020 | Stephenson |
| 2007/0161859 A1 | 7/2007 | Kubach |
| 2009/0225159 A1* | 9/2009 | Schneider .......... A61B 1/00022 348/82 |
| 2010/0068237 A1 | 3/2010 | Li et al. |
| 2011/0104223 A1 | 5/2011 | Li |
| 2012/0041305 A1 | 2/2012 | Grissom et al. |
| 2012/0073614 A1 | 3/2012 | Otani et al. |
| 2015/0238085 A1 | 8/2015 | Inoue et al. |
| 2016/0025653 A1 | 1/2016 | Jalilian et al. |
| 2016/0081531 A1 | 3/2016 | Yoshie |
| 2016/0279658 A1 | 9/2016 | Li et al. |
| 2017/0027420 A1* | 2/2017 | Choi ....................... G01M 3/26 |
| 2017/0332891 A1 | 11/2017 | Yang et al. |
| 2019/0038791 A1* | 2/2019 | Gerrans ................ A61B 90/70 |

FOREIGN PATENT DOCUMENTS

| | | |
|---|---|---|
| CN | 1964665 | 5/2007 |
| CN | 101564545 | 10/2009 |
| CN | 103749445 | 4/2014 |
| CN | 105346758 | 2/2016 |
| CN | 105379712 | 6/2016 |
| CN | 108627519 | 10/2018 |
| DE | 102013202540 A1 | 8/2014 |
| JP | 2971608 | 11/1999 |
| JP | 2005305182 | 11/2005 |
| JP | 2008054861 | 3/2008 |
| JP | 2009039207 A | 2/2009 |
| JP | 2009142490 | 7/2009 |
| JP | 2009165506 | 7/2009 |
| JP | 2009172054 | 8/2009 |
| JP | 2014041043 | 3/2014 |
| KR | 20150123421 A | 11/2015 |
| WO | 2006096797 | 9/2006 |
| WO | 2010129532 | 11/2010 |

OTHER PUBLICATIONS

Peer Contribution by China National Intellectual Property Jan. 16, 2020, of International PCT Application No. PCT/US2019/59364 filed Nov. 1, 2019.

Peer Contribution by European Patent Office Jan. 22, 2020, of International PCT Application No. PCT/US2019/59364 filed Nov. 1, 2019.

Peer Contribution by Japan Patent Office Jan. 24, 2020, of International PCT Application No. PCT/US2019/59364 filed Nov. 1, 2019.

Peer Contribution by Korean intellectual Property Office Jan. 21, 2020, of International PCT Application No. PCT/US2019/59364 filed Nov. 1, 2019.

International Preliminary Report on Patentability issued in PCT/US2019/059364, dated May 20, 2021.

* cited by examiner

ENDOSCOPE CLEANING AND INSPECTION SYSTEM AND METHOD

PRIORITY CLAIM

This application claims priority to and the benefit of U.S. Provisional application with Ser. No. 62/755,829, filed on Nov. 5, 2018, entitled ENDOSCOPE CLEANING AND INSPECTION SYSTEM AND METHOD, which is herein incorporated by reference in its entirety.

TECHNICAL FIELD

Embodiments pertain to the cleaning and reprocessing of reusable medical equipment. Some embodiments more specifically relate to an inspection system and inspection techniques used during cleaning and verification phases of endoscope reprocessing, to assist with removal of biological contaminants and detection of damage and abnormalities.

BACKGROUND

Specific de-contamination procedures and protocols are utilized to clean reusable medical equipment. As one example in the medical setting involving reusable medical equipment, endoscopes that are designed for use in multiple procedures must be fully cleaned and reprocessed after a medical imaging procedure to prevent the spread of infectious organisms. Once an endoscope is used in the medical procedure, an endoscope is considered contaminated until it is properly cleaned and disinfected through a series of specific cleaning actions.

A number of protocols and assisting equipment for cleaning, disinfection, and inspection are used by current medical practices to reprocess endoscopes and prepare them for subsequent procedures. For example, various machines and devices such as automated endoscope reprocessors are used to perform deep cleaning of an endoscope, through the application of disinfecting cleaning solutions. High-level disinfection or sterilization processes are typically performed after manual cleaning to remove any remaining amounts of soils and biological materials. However, an endoscope is not considered as ready for high-level disinfection or sterilization until it has been inspected and verified to function correctly, without any damage or leaking parts. If the endoscope includes damaged surfaces, leaks, broken controls, or the like, the endoscope may not be fully exposed to deep cleaning by the disinfecting chemicals, and the opportunity for spreading contamination significantly increases.

During existing manual cleaning procedures, a human technician may inspect the endoscope for damage and perform various types of inspections, verifications, or tests on the external surfaces and operational components of the endoscope. However, many types of contaminants and damage within the endoscope are not readily visible or observable by a human. Therefore, there is a need to improve cleaning processes of endoscopes to reduce the incidence and amount of residual biological material, as well as a need to improve inspection processes to detect residual biological material or damage to the endoscope.

BRIEF DESCRIPTION OF THE DRAWINGS

FIG. 8 is a block diagram illustrating an architecture for an example computing system used in accordance with some embodiments.

DETAILED DESCRIPTION

Figure 1:
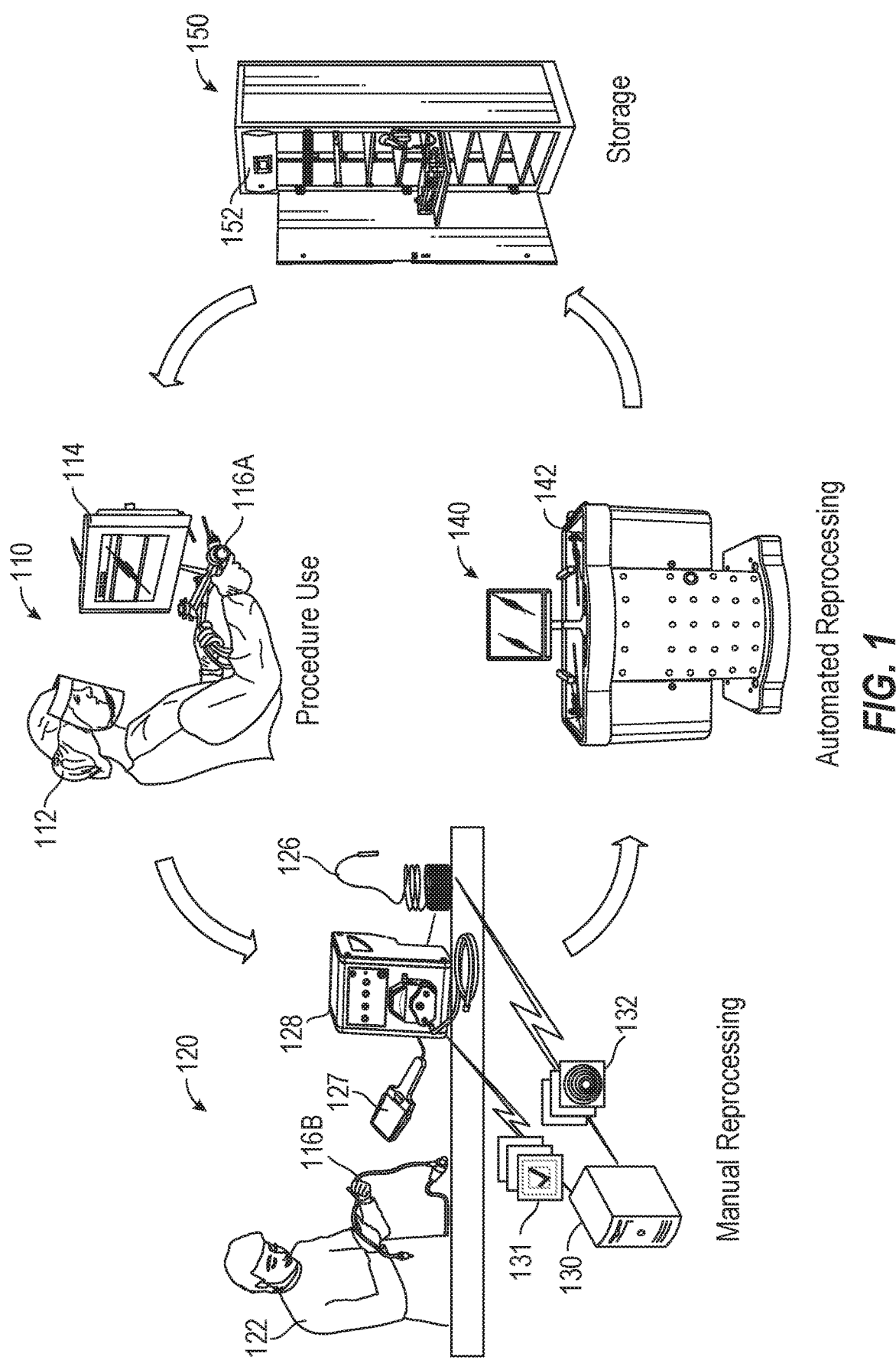
FIG. 1 illustrates an overview of devices and systems involved in stages of endoscope use and reprocessing, according to various examples discussed herein.

The following description and the drawings sufficiently illustrate specific embodiments to enable those skilled in the art to practice them. Other embodiments may incorporate structural, logical, electrical, process, and other changes. Portions and features of some embodiments may be included in, or substituted for, those of other embodiments. Embodiments set forth in the claims encompass all available equivalents of those claims.

Various techniques and devices configured for the management of cleaning, testing, inspection, and verification of a reusable medical equipment, such as an endoscope, are described herein. Specifically, aspects of an endoscope cleaning and inspection system are described to facilitate and improve aspects of manual cleaning, which have been conventionally performed by basic devices and manual human involvement. As discussed herein, the endoscope cleaning and inspection system may be embodied through integrated, standalone equipment (e.g., a single device) or coordinated devices or components (e.g., independent devices which are operably coupled to one another in a system) to perform the described functionality. As a result, references to a cleaning and inspection "system" or a respective cleaning and inspection "device" may encompass many different form factors that involve a single or multiple physical units. Further, the implementation of such a system or respective devices may involve the integration of a single or multiple unit(s), machine(s), device(s), computing system(s), or like electronic or mechanical apparatus(es).

In an example, an endoscope cleaning and inspection system is described which includes capabilities in an integrated unit for leak testing, fluid cleaning, visualization, and inspection as part of an endoscope reprocessing protocol that occurs separately from (typically, before) automated reprocessing. This integrated unit is referred to in many of the following examples as a "testing and cleaning unit". For instance, aspects of leak testing may be performed by the integration of leak test equipment to verify that endoscope channels and components maintain fluid pressure integrity. Aspects of fluid cleaning may include the controlled or coordinated use of internal channel (e.g., interior lumens or passageways of the endoscope) flushing using detergents and other chemical compositions. Aspects of visualization may include the use of a borescope or other visual inspection mechanism which may be directed into channels of an endoscope to capture an optical view (and, in some examples, capture image data) to identify a condition or state of the interior endoscope channels. Aspects of inspection may include the use of an optical magnifier or like inspection enhancement tool which may be exposed to the exterior surface of an endoscope to capture an enlarged optical view (and, in some examples, capture enlarged image data) to identify a condition or state of the exterior endoscope surfaces or components. Accordingly, many aspects of the endoscope cleaning and inspection system may replace procedures or tooling previously provided by separate devices and manual human activity in a reprocessing protocol or cleaning workflow.

In a further example, aspects of automation and enhanced logic may be integrated into the endoscope cleaning and inspection system, to allow advanced verification of cleaning operations and the identification and tracking of inspection conditions or states. This may include integration with a visual inspection processing system, which may employ artificial intelligence analysis to identify damage from an endoscope channel based on image data captured by a borescope. For instance, a trained machine learning model may be used to analyze the image data and classify damage or abnormal states of an endoscope channel. The logic and functionality to implement the visual inspection processing system may be implemented directly within a device of the endoscope cleaning system (e.g., such as in a testing and cleaning unit). In other examples, one or more devices of the endoscope cleaning system (e.g., the testing and cleaning unit, a connected borescope, or a connected image capture device) may be used to communicate the image data to the visual inspection processing system located at an external location (e.g., at a remote network). Any detected status of damage, contamination, leaks, or the successful performance of cleaning and inspection actions, may be communicated to a tracking system to enable verification and further analysis of the state of the endoscope reprocessing from what would otherwise be manual activities.

One of the presently described form factors of the cleaning and inspection system includes a cleaning and testing unit that controls leak testing equipment, flush control equipment, and optical inspection equipment, from a single device housing. In this example, the unit includes one or more fluid connector to connect an endoscope to the leak testing and flush control equipment, electrical connections to connect to optical inspection equipment, and an output screen to output the status and results of the leak testing, flushing, and optical inspection. This integration into a single unit addresses a common lack of space in reprocessing facilities for handling endoscopes. Specifically, this integration combines the relevant technology in one unit and reduces the overall space needed to perform the respective functions, in a form factor which may be hosted or mounted in a more convenient location (e.g., on a shelf, wall, cart, etc.). This provides a significant space and operational benefits over current settings where separate testing, flushing, and inspection devices are used in limited spaces.

The presently described cleaning and testing unit may support multiple types of inspection equipment, including a borescope (for inspection of an internal lumen of the endoscope) and a magnifier (for inspection of an external surface or externally-visible structure of the endoscope). In contrast, current uses of borescopes typically involve a large, separated monitor which may be difficult to handle in at a cleaning workstation or sink. Further, the use of an external magnifier provides a significant benefit over current human inspection processes, allowing a user to capture and enlarge small areas on the external surfaces or components of the scope for viewing and analysis. The testing and cleaning unit may also provide a common output screen for the external magnifier output, to allow a user to easily capture and store images from the magnifier output.

With the use of a common endoscope cleaning and inspection system, all data relating to manual reprocessing procedures, test results, and internal and external inspection visualizations, may be controlled, viewed, captured, and tracked from one integrated location. As a result, the presently described techniques and configurations enhance many aspects of manual cleaning activities within device reprocessing workflows, to provide consistent and repeatable processes and increase the accuracy of cleaning operations. Such aspects provide not only automation and data tracking benefits, but also result in improved cleaning results and a reduction in contamination (and cross-contamination), increased identification of defects and damage of the equipment, and improved performance of cleaning activities far beyond human capabilities.

FIG. 1 illustrates an overview of devices and systems involved in example stages of endoscope use and reprocessing. In the environment illustrated in FIG. 1, a series of stages are sequentially depicted for use and handling of the endoscope, transitioning from a procedure use stage 110, to manual reprocessing stage 120, to an automated reprocessing stage 140, to a storage stage 150. It will be understood that the stages 110, 120, 140, 150 as depicted and described provide a simplified illustration of typical scenarios in the use, handling, and reprocessing for reusable endoscopes. As a result, many additional steps and the use of additional devices and procedures (or, substitute procedures and substitute devices) may be involved in the respective stages.

The procedure use stage 110 depicts a human user 112 (e.g., technician, nurse, physician, etc.) who handles an endoscope. At the commencing of the procedure use stage 110, the endoscope 116A is obtained in a sterile or high-level disinfected/clean state. This disinfected/clean state typically results from reprocessing and storage of the endoscope 116A, although the state may also be provided from a disinfected repair or factory-provided state (not shown). In the procedure use stage 110, the endoscope 116A may be used for various endoscopic procedures (e.g., colonoscopy, upper endoscopy, etc.) on a subject human patient, for any number of diagnostic or therapeutic purposes. During the endoscopic procedures, the endoscope 116A is exposed to biological material from the subject patient or the surrounding environment. Thus, at the completion of the procedure use stage 110, the endoscope 116A exists in a contaminated state.

The disinfected or contamination state of the endoscope 116A may be tracked by a tracking system for purposes of monitoring, auditing, and other aspects of workflow control. An interface 114 to the tracking system is shown, which receives an identifier of the endoscope 116A and provides a graphical status as output. The tracking system may be used in the procedure use stage 110 (and the other stages 120, 140, 150) to identify the use of the endoscope 116A to be associated with a particular imaging procedure, patient, procedure equipment, procedure room, preparation or cleaning protocol, or other equipment or activities. This identifying information may enable the tracking system to track the contamination or disinfected state of the endoscope, and to identify and prevent exposure of contamination or infectious agents to patients or handling personnel from damaged endoscopes or improper cleaning procedures.

After the procedure use stage 110, the endoscope transitions to handling in a manual reprocessing stage 120. The manual reprocessing stage 120 specifically depicts the use of manual cleaning activities being performed by a technician 122, to clean the endoscope 116B. The type of manual cleaning activities may include use of disassembly and removal of components, applying brushes to clear channels, wiping to remove visible liquids and solids, and other human-performed cleaning actions. Some of the manual cleaning activities may occur according to a regulated sequence or manufacturer-specified instructions.

The manual reprocessing stage 120 also depicts the use of a cleaning and inspection system, involving a borescope 126, a visual magnification device 127, and a testing and cleaning unit 128 to conduct additional aspects of cleaning and inspection. In an example, the testing and cleaning unit 128 is operable to perform an initial chemical flush of the internal channels of the endoscope 116B (e.g., water, air, or suction channels) with cleaning agents. The testing and cleaning unit 128 also enables the performance of leak testing, to verify whether components or structures of the endoscope leak fluid (e.g., leak water or air). Data 131 which indicates a status of the leak test, flushing, or other cleaning and inspection procedures may be provided to a computing system 130 for processing and analysis. The results of the leak testing and the flushing may be tracked or managed as part of a device tracking or cleaning workflow.

In an example, the borescope 126 is used as part of an inspection procedure controlled by the endoscope cleaning and inspection system, and used to inspect an interior lumen of a channel in the endoscope 116B. This may include the inspection of a channel of the endoscope 116B used for biopsy and instrument insertion. The borescope 126 may be inserted and advanced by a human or a machine within one or more lumens (e.g., openings defined by channels, cavities, or other internal spaces) of the endoscope 116B to perform the inspection procedure. This inspection procedure may occur before or after the performance of the leak test, flushing, or other cleaning or testing activities in the manual reprocessing stage 120.

The borescope 126 may produce image data 132 (e.g., one or more images, such as a video) that provide a detailed, high-resolution view of the status of a channel of the endoscope 116B. The image data 132 may be provided to a computing system 130 (e.g., provided through the testing and cleaning unit 128, or from the borescope 126 directly) for processing and analysis. The borescope 126 may be operated as part of a borescope inspection system, which provides controlled or mechanicalized advancement and movement of the borescope 126 in an inspection procedure. The results of the borescope inspection procedure may be tracked or managed as part of a device tracking or cleaning workflow, including with the aforementioned tracking system.

In an example, the computing system 130 is provided by a visual inspection processing system that uses a trained artificial intelligence (e.g., machine learning) model to analyze image data 132 and identify a state of the endoscope channel. For instance, the state of the endoscope channel may include, no detected abnormalities (e.g., an integrity state), or a detected presence of biological material or a detected presence of channel damage (e.g., a compromised state). Further examples of the borescope inspection system and the visual inspection processing system are referenced in the discussed examples below.

In an example, the visual magnification device 127 is provided in a handheld form factor, with the device including an output screen on a first side (top side) which provides an expanded/exploded view of a captured area observed from a camera on a second opposite side (bottom side) using optical and image processing techniques. The visual magnification device 127 may include a handle or other user-operated structure to allow simple movement of the device to image different areas of the endoscope. The visual magnification device 127 may include a camera imaging sensor (e.g., CCD/CMOS sensor) and lens, imaging processing circuitry to capture and magnify the image data, and controls to control magnification, capture, or the display of magnified images. For instance, the visual magnification device 127 may provide between 2-20× magnification of an imaged area using any combination of optical lenses and digital image enhancement techniques. The visual magnification device 127 may be electrically coupled to the testing and cleaning unit 128 to receive power and communicate data and controls. The enlarged imaging captured from the visual magnification device 127 may also be output in real-time to the screen of the testing and cleaning unit 128 and controlled from such unit. For instance, use of the visual magnification device 127 may allow a user to perform a detailed inspection of the flexible portion(s) of the endoscope, electrical connections, chips and scratches on cover glasses, and adhesive rings or seals, any of which may degrade over time. Further, the visual magnification device 127 may allow a user to identify biofilm formation or the presence of visible contamination.

In an example, the testing and cleaning unit 128 is operably coupled (e.g., with a wireless or wired communication channel) with each of the visual magnification device 127, the borescope 126, and the visual processing system 130. The flushing and leak testing unit 128 may also include an input device, output device, control logic, and other processing logic to enable or control operation of the connected devices. As a result, many functions and components of the endoscope cleaning and inspection system presently discussed herein may be provided directly within the flushing and leak testing unit (e.g., by the same machine). Further embodiments and features of the testing and cleaning unit 128 are discussed below with reference to FIG. 5.

After completion of the manual reprocessing stage 120, the endoscope is handled in an automated reprocessing stage 140. This may include the use of an automatic endoscope reprocessor (AER) 142, or other machines which provide a high-level disinfection or sterilization of the endoscope. For instance, the AER 142 may perform disinfection for a period of time (e.g., for a period of minutes) to expose the interior channels and exterior surfaces of the endoscope to deep chemical cleaning and disinfectant solutions. The AER 142 may also perform rinsing procedures with clean water to remove chemical residues.

After completion of the automated reprocessing stage 140 and the production of the endoscope in a disinfected state, the endoscope transitions to handling in a storage stage 150. This may include the storage of the endoscope in a sterile storage unit 152. In some examples, this stage may also include the temporary storage of the endoscope in a drying unit. Finally, retrieval of the endoscope from the storage stage 150 for use in a procedure results in transitioning back to the procedure use stage 110.

The overall cleaning workflow provided for an endoscope within the various reprocessing stages 120 and 140 may vary according to the specific type of device, device-specific requirements and components, regulations, and the types of cleaning chemicals and devices applied. However, the overall device use and cleaning workflow, relative to stages of contamination, may be generally summarized in stages 110, 120, 140, 150, as involving the following steps:

1) Performance of the endoscopic procedure. As will be well understood, the endoscopic procedure results in the highest amount of contamination, as measured by the amount of microbes contaminating the endoscope.

2) Bedside or other initial post-procedure cleaning. This cleaning procedure removes or reduces the soils and biological material encountered on the endoscope during the endoscopic procedure. As a result, the amount of contamination, as measured by the amount of microbes, is reduced.

3) Transport to reprocessing. The more time that is spent between the procedure and reprocessing results in a potential increase in the amount of contamination or difficulty to remove the contamination, due to biological materials drying, congealing, growing, etc.

4) Performance of a leak test (e.g., conducted in the manual reprocessing stage 140 with the integrated testing and cleaning unit 128 or a standalone leak testing device or procedure (not shown)). This leak test is used to verify if any leaks exist within channels, seals, controls, valve housings, or other components of the endoscope. If the endoscope fails the leak test, or encounters a blockage during flushing, then high-level disinfection or sterilization attempted in automated reprocessing will be unable to fully flush and disinfect all areas of the endoscope. Further, if the leak test fails but the instrument is placed in an automatic reprocessing machine, the instrument will be damaged through fluid ingress during the reprocessing cycle.

5) Manual washing (e.g., conducted in the manual reprocessing stage 140 with brushes, flushing, etc., including a chemical flush performed by the integrated testing and cleaning unit 128). This aspect of manual washing is particularly important to remove biofilm and lodged biological agents from spaces on or within the endoscope. Biofilm generally refers to a group of microorganisms that adheres to a surface, which may become resistant or impervious to cleaning and disinfectant solutions. The successful application of manual washing significantly reduces the amount of contamination on the endoscope.

6) Damage inspection (e.g., conducted in manual reprocessing stage 140 with a borescope and magnification device, such as enabled by use of optical inspection equipment with the integrated testing and cleaning unit 128). Microbes and in particular biofilm may resist cleaning if lodged in damaged or irregular portions of the endoscope. A procedure of damage inspection can be used to identify surface irregularities, scratches and fissures, or other defects or abnormal states (e.g., a compromised state) within the interior channels, exterior surfaces, or components of the endoscope. This damage inspection may also be accompanied by the detection of biological materials (such as biofilms) which remain after manual washing.

7) High level disinfection or sterilization (e.g., conducted in AER 142). Upon successful conclusion of the high-level disinfection or sterilization process, in an ideal state for an endoscope with no damage, no biological contamination will remain from the original endoscopic procedure.

8) Rinse and Air Purge. This stage involves the introduction of clean water and air, to flush any remaining chemical solution and to place the endoscope in a disinfected and clean state. The risk of introducing new contamination may be present if contaminated water or air are introduced to the endoscope.

9) Transport to Storage. This stage involves the transport from the AER or other device to storage. A risk of introducing new contamination may be present based on the method and environment of transport and handling.

10) Storage. This stage involves the storage of the endoscope until needed for a procedure. A risk of introducing new contamination may be present based on the conditions in the storage unit.

11) Transport to Patient. Finally, the endoscope is transported for use in a procedure. A risk of introducing new contamination may also be present based on the method and environment of transport and handling.

Further aspects that affect contamination may involve the management of valves and tubing used with a patient. For instance, the use of reusable valves, tubing, or water bottles in the procedure may re-introduce contamination to the endoscope. Accordingly, the disinfected state of a processed endoscope can only be provided in connection with the use of other sterile equipment and proper handling in a clean environment.

As will be well understood, the aspects of the manual reprocessing stage in conventional settings involves a large amount of risks, as it is a human-controlled stage and each step involves many different actions. The presently described endoscope cleaning and inspection system integrates these actions into control from a single unit to create a consistent process for the user. Additionally, in conventional settings, users do not have assurance upon completion of manual cleaning whether contaminants still may exist. The integration of optical inspection features and tracking into the cleaning and inspection system enables both dynamic indication and tracking to handle cases where an endoscope has been fully cleaned or still includes contaminants or damaged areas.

Figure 2:
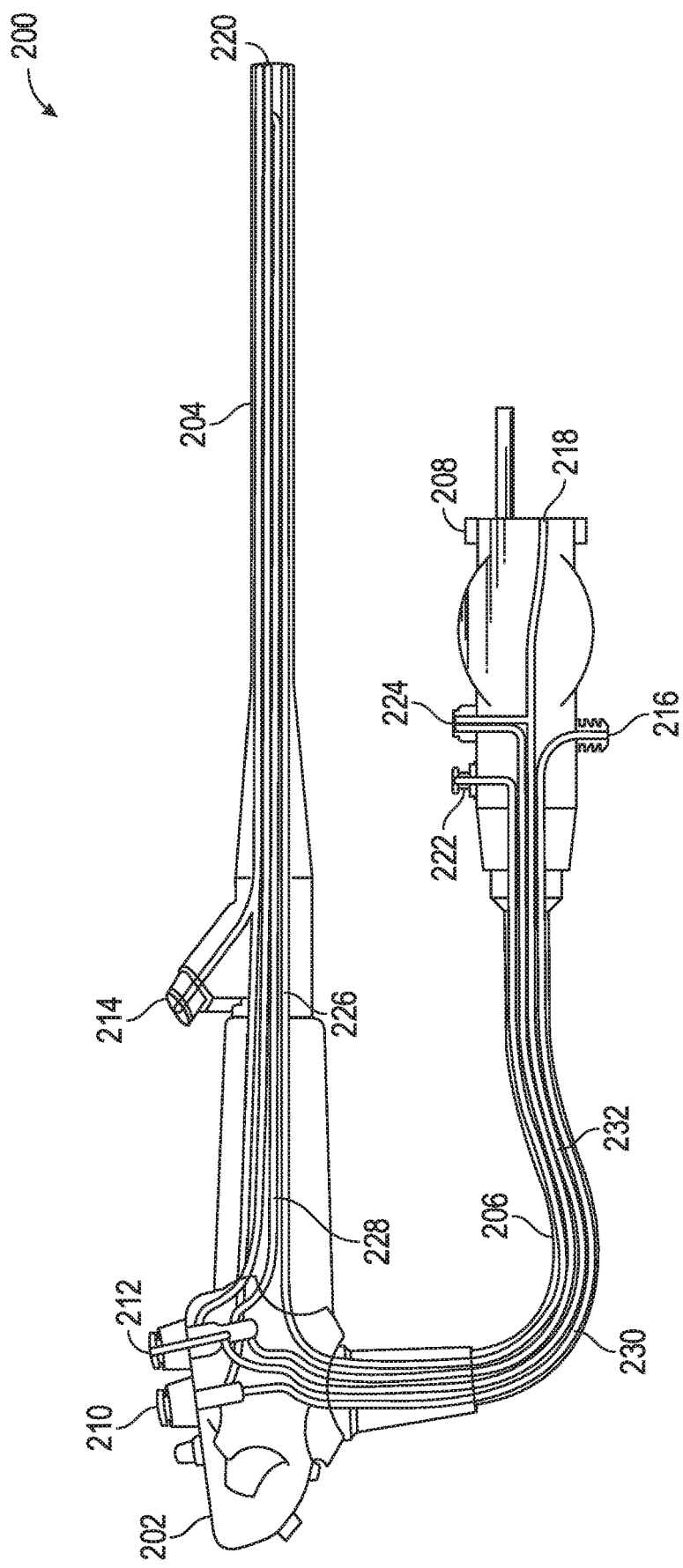
FIG. 2 is a schematic cross-section illustration of an endoscope, operated according to various examples discussed herein.

FIG. 2 is a schematic cross-section illustration of an endoscope 200, operable according to various examples. The endoscope 200 as depicted includes portions that are generally divided into a control section 202, an insertion tube 204, a universal cord 206, and a light guide section 208. A number of imaging, light, and stiffness components and related wires and controls used in endoscopes are not depicted for simplicity. Rather, FIG. 2 is intended to provide a simplified illustration of the channels important for endoscope cleaning workflows. It will be understood that the presently discussed endoscope cleaning workflows will be applicable to other form factors and designs of endoscopes. The techniques, systems, and apparatus discussed herein can also be utilized for inspection operations on other instruments that include lumens that can become contaminated or damaged during use.

The control section 202 hosts a number of controls used to actuate the positioning, shape, and behavior of the endoscope 200. For instance, if the insertion tube 204 is flexible, the control section 202 may enable the operator to flex the insertion tube 204 based on patient anatomy and the endoscopic procedure. The control section 202 also includes a suction valve 210 allowing the operator to controllably apply suction at a nozzle 220 via a suction channel 230. The control section 202 also includes an air/water valve 212 which allows the distribution of air and/or water from an air channel 232 (provided from an air pipe source 218) or a water channel 228 (provided from a water source connected to a water source connector 224) to the nozzle 220. The depicted design of the endoscope 200 also includes a water jet connector 222 via a water-jet channel 226, to provide additional distribution of water separate from the air channel 232.

The universal cord 206 (also known as an "umbilical cable") connects the light guide section 208 to the control section 202 of the endoscope. The light guide section 208 provides a source of light which is distributed to the end of the insertion tube 204 using a fiber optic cable or other light guides. The imaging element (e.g. camera) used for capturing imaging data may be located at in the light guide section 208 or adjacent to the nozzle 220.

As shown, the various channels of the endoscope 200 allow the passage of fluids and objects, which may result in the contamination throughout the extent of the channels. The portion of the suction channel 230 which extends from the biopsy valve 214 to the distal end of the insertion tube 204 (to the nozzle 220) is also known as the biopsy channel. In particular, the biopsy channel, and the remainder of the suction channel 230, is subject to a high likelihood of contamination and/or damage in the course of an endoscopic procedure. For example, the insertion, manipulation, and extraction of instruments (and biological material attached to such instruments) through the suction channel 230 commonly leads to the placement of microbes within the suction channel 230.

Any damage to the interior layer(s) of the biopsy channel, such as in scratches, nicks, or other depressions or cavities to the interior surface caused by instruments moving therein may also lead to deposits of biological material. Such biological material which remains in cavities, or which congeals in the form of biofilm, may be resistant to many manual cleaning techniques such as brushes pulled through the suction channel Such damage may also occur in the other channels 228, 230, 232, as a result of usage, deterioration, or failure of components. The techniques discussed herein provide enhanced techniques in connection with the inspection and verification of the integrity of the channels 228, 230, 232, including integrity from damages or defects, and/or integrity from deposited biological materials and contamination.

Figure 3:
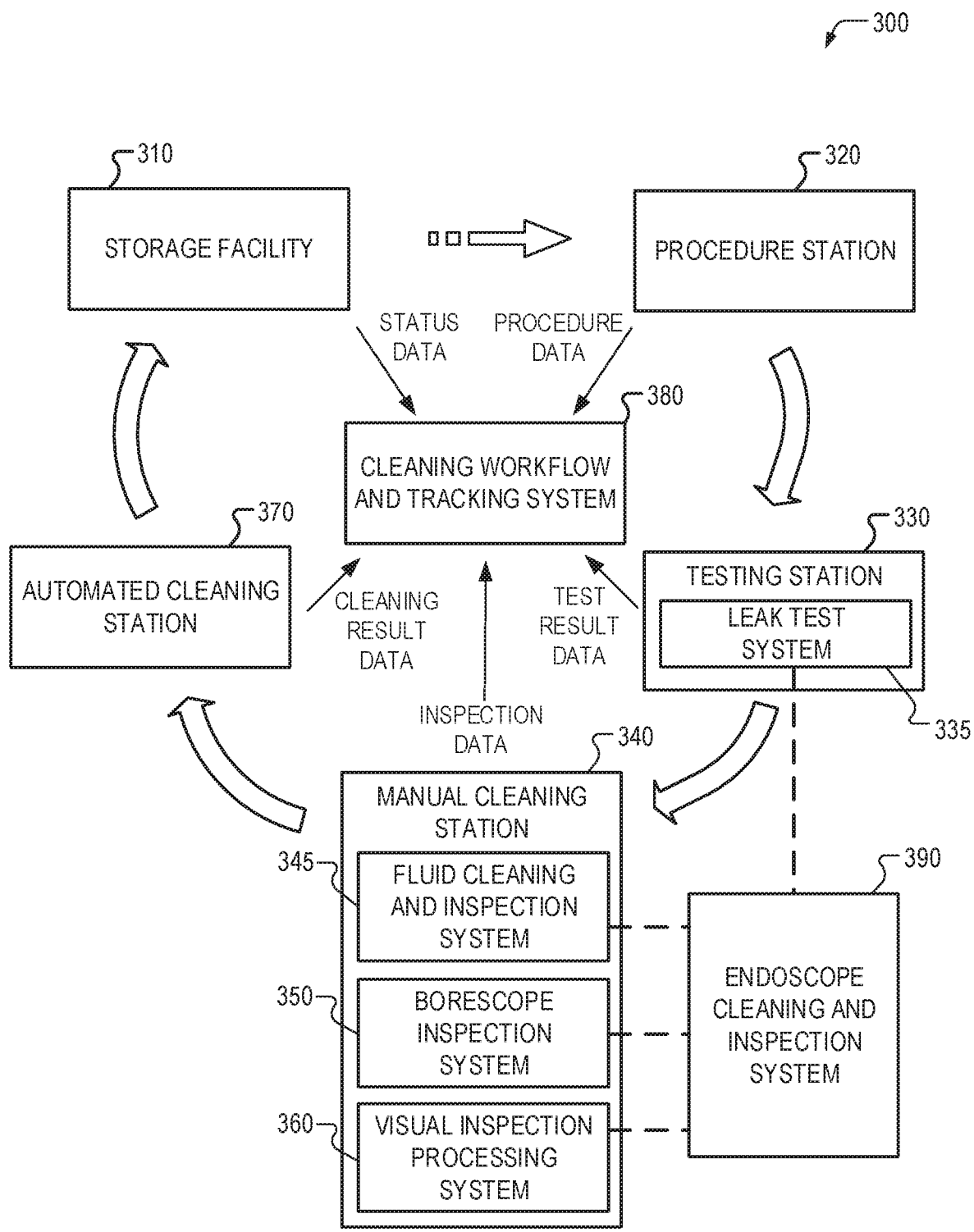
FIG. 3 illustrates data flows provided with a cleaning workflow and tracking system, during respective stages of endoscope use and processing, according to various examples discussed herein.

FIG. 3 illustrates data flows 300 provided with an example cleaning workflow and tracking system 380, during respective stages of endoscope use and processing. The data flows 300 depict the collection of data from an endoscope cleaning and inspection system 390 that integrates use of a leak test system 335, fluid cleaning and inspection system 345, borescope inspection system 350, and visual inspection processing system 360, to clean and perform an integrity verification of one or more endoscope channels and components.

Although the leak test system 335, fluid cleaning and inspection system 345, borescope inspection system 350, and visual inspection processing system 360 are depicted as separate systems, it will be understood that such systems may be operated as components under the control and orchestration of the endoscope cleaning and inspection system 390. For instance, the leak test system 335 may comprise air pumps, pressure sensors, and measurement gauges hosted or controlled within a common device (e.g., the integrated testing and cleaning unit 128); the fluid cleaning and inspection system 345 may comprise fluid pumps, chemical tanks, and chemical measurement sensors hosted or controlled within the common device (e.g., the integrated testing and cleaning unit 128); the borescope inspection system 350 may comprise an optical probe and imaging unit, configured to provide imaging output to the integrated testing and cleaning unit 128, as captured from within an endoscope lumen (e.g., with imaging data is captured, controlled, and displayed by the integrated testing and cleaning unit 128); and the visual inspection processing system 360 may comprise an artificial intelligence functionality hosted within or invoked by the cleaning workflow and tracking system 380, to analyze inspection imaging data from the borescope inspection system 350 or other visual inspection components. A magnification inspection system, not shown, also may be integrated at the manual cleaning station 340 and provide imaging output to the integrated testing and cleaning unit 128, as captured from an externally visible area of the lumen (e.g., as imaging data is captured, controlled, and displayed by the integrated testing and cleaning unit 128).

The data flows 300 specifically illustrate the generation and communication of data as the endoscope is handled or used at various locations. These include: status of the endoscope at a storage facility 310 (e.g., the storage unit 152 in the storage stage 150), as indicated via status data (e.g., a location and sterilization status of the endoscope); status of the use of the endoscope at a procedure station 320 (e.g., as handled in the procedure use stage 110), as indicated via procedure data (e.g., an identification of a patient, physician, and handling details during the procedure); status of the testing of the endoscope at a testing station 330 (e.g., with a leak test performed with a leak test system 335, such as incorporated into the testing and cleaning unit 128), as indicated via test result data (e.g., a pass or fail status of a test, measurement values, etc.); status of the manual cleaning actions performed at a manual cleaning station 340 (e.g., with a chemical flush performed with a fluid cleaning and inspection system 345, such as incorporated into the testing and cleaning unit 128), as indicated by inspection data (e.g., a status that logs the timing and result of inspection procedures, cleaning activities); and a status of the machine cleaning actions performed at an automated cleaning station 370 (e.g., as performed by the AER 124), as indicated by cleaning result data (e.g., a status that logs the procedures, chemicals, timing of automated reprocessing activities). Such statuses and data may be communicated for storage, tracking, maintenance, and processing, at a cleaning workflow and tracking system 380 (and databases operated with the system 380).

The location of the endoscope among the stations, and activities performed with the endoscope, may be performed in connection with specific device handling workflow. Such a workflow may include a step-by-step cleaning procedure, maintenance procedures, or a tracking workflow, to track and manage a disinfected or contaminated status, operational or integrity status, or cleaning procedure status of the endoscope components or related equipment. In connection with testing operations at the testing station 330, or cleaning operations at the manual cleaning station 340 or the automated cleaning station 370, the subject endoscope may be identified using a tracking identifier unique to the endoscope, such as a barcode, RFID tag, or other identifier coupled to or communicated from the endoscope. For instance, the testing station 330 or manual cleaning station 340 (e.g., using the endoscope cleaning and inspection system 390), or the automated cleaning station 370, may host an identifier detector to receive identification of the particular endoscope at the respective station. In an example, the identifier detector comprises a RFID interrogator or bar code reader used to perform hands-free identification.

Additionally, in connection with a cleaning workflow, tracking workflow, or other suitable device handling workflow, a user interface may be output to a human user via a user interface device (e.g., a display screen, audio device, or combination). For example, the user interface may request input from the human user to verify whether a particular cleaning protocol has been followed by the human user at each of the testing station 330, manual cleaning station 340, and automated cleaning station 370. A user interface may also output or receive modification of the status in connection with actions at the storage facility 310 and the procedure station 320. The input to such user interface may include any number of touch or touch-free (e.g., gesture, audio command, visual recognition) inputs, such as with the use of touchless inputs to prevent contamination with an input device. Such user interface may be provided through the endoscope cleaning and inspection system 390 (e.g., through use of the integrated testing and cleaning unit 128).

In various examples, input recognition used for control or identification purposes may be provided within logic or devices of any of the stations 310, 320, 330, 340, 370, or as interfaces or controls to the endoscope cleaning and inspection system 390. In still further examples, tracking of patients, cleaning personnel, technicians, and users or handlers of the endoscope may be tracked within the data values communicated to the cleaning workflow and tracking system 380. The interaction with the cleaning workflow and tracking system 380 may also include authentication and logging of user identification information, including validation of authorized users to handle the device, or aspects of user-secure device reprocessing and servicing.

A variety of inquiries, prompts, or collections of data may occur at various points in a device cleaning or handling workflow, managed by the cleaning workflow and tracking system 380, to collect and output relevant data. Such data may be managed for procedure validation or quality assurance purposes, for example, to obtain human verification that a cleaning process has followed proper protocols, or that human oversight of the cleaning process has resulted in a satisfactory result. Workflow steps may also be required by the workflow and tracking system 380 to be performed in a determined order to ensure proper cleaning, and user inquiries and prompts may be presented in a determined order to collect full information regarding compliance or procedure activities. Further, the cleaning workflow and tracking system 380 may be used to generate an alert or display appropriate prompts or information if a user or device does not fully completion certain steps or procedures.

Figure 4:
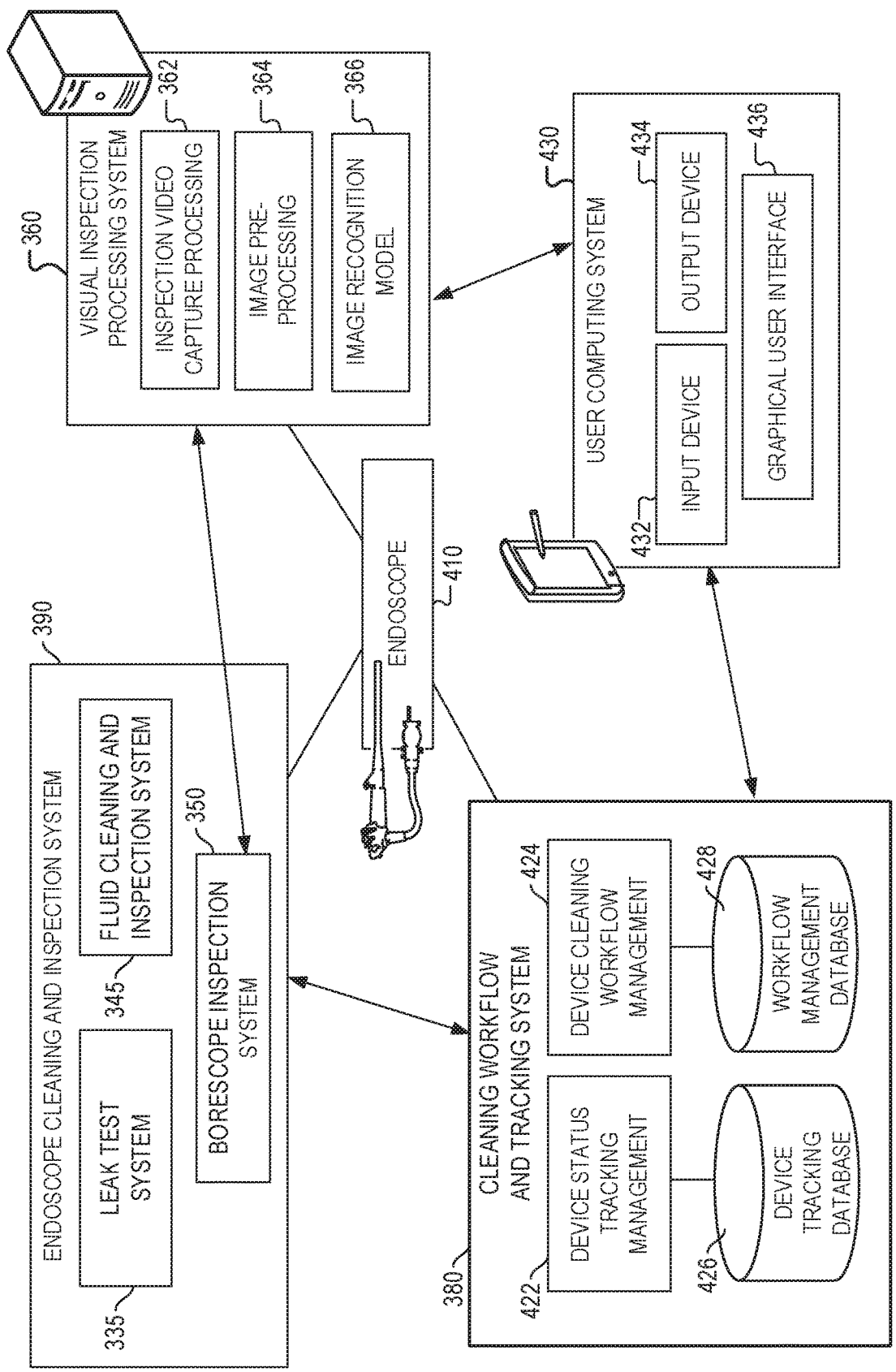
FIG. 4 is a block diagram of system components used to interface among tracking and inspection systems and devices, according to various examples discussed herein.

FIG. 4 is a block diagram of system components used to interface among example imaging, tracking, and processing systems. As shown, the components of the endoscope cleaning and inspection system 390 may include the leak test system 335, the fluid cleaning and inspection system 345, and the borescope inspection system 350. In this block diagram, the borescope inspection system 350 may provide video or imaging output from the imaging of internal channels of the endoscope 410, for use in the endoscope cleaning and inspection system (e.g., for output on a display screen included in the system 390), or for use and analysis by another system (e.g., by the visual inspection processing system 360). In other examples, not depicted, features of the visual inspection processing system 360 may be included within the cleaning and inspection system 390.

The cleaning workflow and tracking system 380 may include functionality and processing components used with a variety of cleaning and tracking purposes involving the endoscope 410. Such components may include device status tracking management functionality 422 that utilizes a device tracking database 426 to manage data related to status(es) of contamination, damage, tests, and usage for the endoscope 410 (e.g., among any of the stages 110, 120, 140, 150). Such components may also include a device cleaning workflow management functionality 424 used to track cleaning, testing, verification activities, initiated as part of a cleaning workflow for the endoscope 410 (e.g., among the reprocessing stages 120, 140). As specific examples, the workflow management database 428 may log the timing and performance of specific manual or automatic cleaning actions, visual inspections performed with a borescope or magnifier, the particular amount or type of cleaning or disinfectant solution applied, which user performed the cleaning action, and the like.

The data and workflow actions in the cleaning workflow and tracking system 380 may be accessed (e.g., viewed, updated, input, or output) through use of a user computing system 430, such as with an input device 432 and output device 434 of a personal computer, tablet, workstation, or smartphone, operated by an authorized user. The user computing system 430 may include a graphical user interface 436 to allow access to the data and workflow actions before, during, or after any of the handling or cleaning stages for the endoscope 410 (e.g., among any of the stages 110, 120, 140, 150). For instance, the user computing system 430 may display a real-time status of whether the endoscope 410 is disinfected, which tests have been completed and passed during cleaning, and the like.

The visual inspection processing system 360 is shown as including functionality and processing components for the analysis of data from the borescope inspection system 350, or other visual inspection components. For instance, video captured by a borescope imaging device 352, advanced within a channel of the endoscope 410 at a particular rate by human insertion or a movement control device, may be captured (and optionally, analyzed) in real-time through use of inspection video capture processing 362. The respective images or video sequences captured are subjected to image pre-processing 364, such as to enhance, crop, or modify images from the borescope imaging device 352. Finally, respective images or sequences of images are input into an image recognition model 366 for computer analysis of the integrity state of the captured channel. The visual inspection processing performed by the processing system 360 may occur in real time with coordinated use (and potentially, automated or machine-assisted control) of the borescope inspection system 350, or as part of a subsequently performed inspection procedure.

In an example, the image recognition model 366 may be a machine-learning image classifier which is trained to identify normal (full integrity) conditions of an imaged channel lumen, versus abnormal (compromised integrity) conditions of the imaged channel state (e.g., lumen). Such abnormal conditions may include the existence of damage or defects to the lumen, the deposit of biological material within the lumen, etc. Other types and forms of artificial intelligence processing may also be used in combination with the image recognition model 366. The results (e.g., classification or other data outputs) from the image recognition model 366 may be output via the user computing system 430 or recorded in the cleaning workflow and tracking system 380.

Other information from components of the endoscope cleaning and inspection system 390, such as from the leak test system 335 and fluid cleaning and inspection system 345, may be maintained with the cleaning workflow and tracking system 380. Further, image or status data from other components of the system 390 (e.g., the magnification system, other test devices, etc.) may also be tracked and used to cause dynamic or automated actions.

Figure 5:
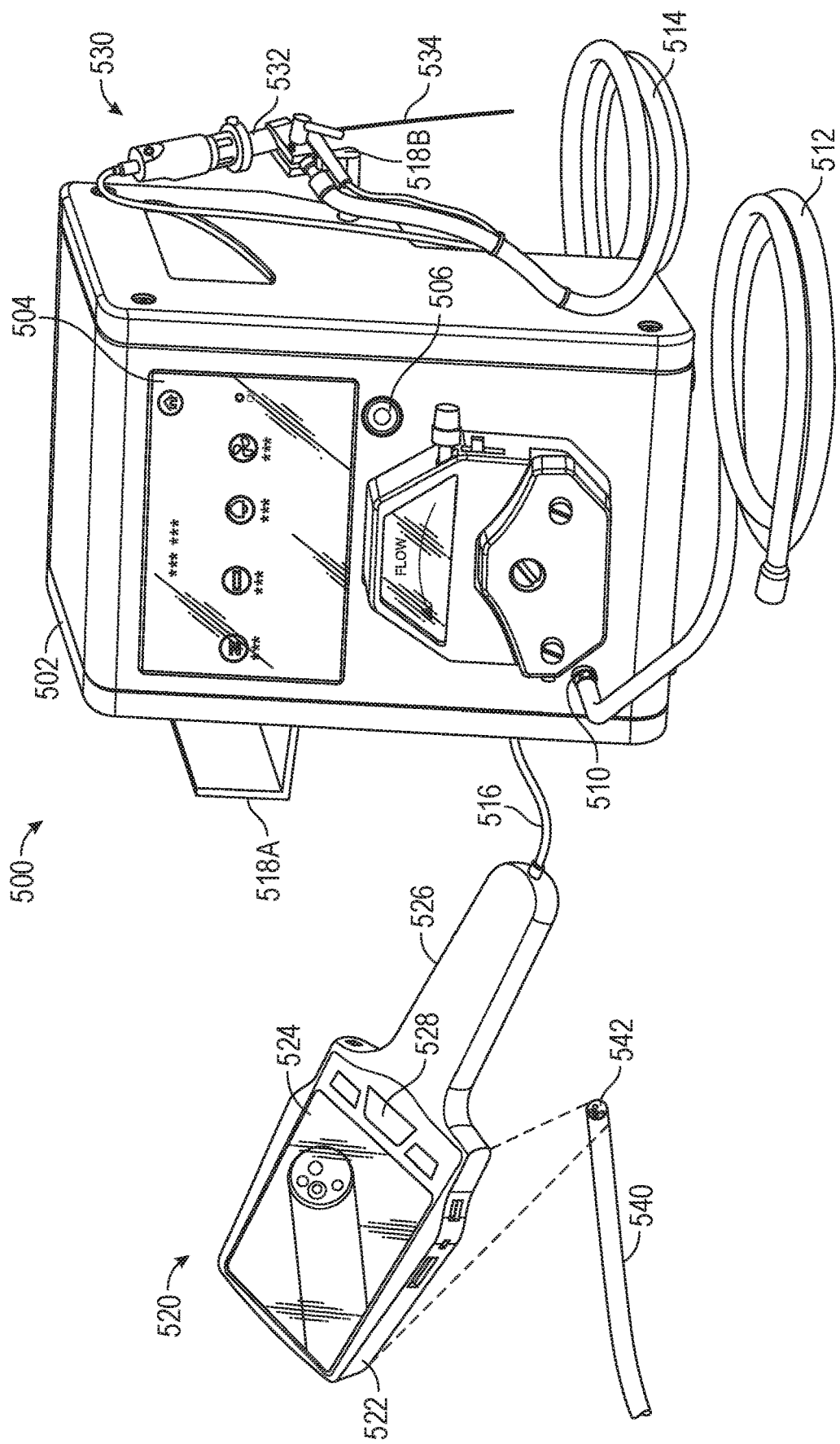
FIG. 5 illustrates an example endoscope cleaning and inspection system integrating leak testing, flushing, and optical inspection features, according to various examples discussed herein.

FIG. 5 illustrates an example implementation of an endoscope cleaning and inspection system integrating leak testing, flushing, and optical inspection features. As shown, the system includes an example endoscope testing and cleaning unit 500, providing a housing 502 that hosts a display screen 504 and fluid connector 510, and which includes an operational control unit (not shown) within the housing 502. The housing 502 may expose user-facing controls such as a control button 506 used to select, start, or stop functions with the unit 500. The control button 506 is shown as being provided as a dedicated control, but it will be understood that the control button 506 may be hosted in a capacitive or resistive touch screen of the display screen 504. Various other electromechanical controls, actuators, and gauges may also be disposed on the housing 502 or within the unit 500.

The fluid connector 510 is illustrated as being coupled to tubing 512, with this tubing including an end that is adapted to couple to a connection port of an endoscope (not shown). For instance, the tubing 512 may removably couple to one or more access ports of a subject endoscope, to allow fluid access to the internal channel(s) (e.g., lumen) of the subject endoscope, in which leak testing, chemical flushing, and other cleaning and testing actions may be performed.

The leak test equipment integrated within the testing and cleaning unit 500 may be controlled with use of the control unit. The leak test equipment may perform a leak test of the internal lumen of the subject endoscope using fluid pressure, and output a result of the leak test on the display screen 504. In an example, the leak test equipment may include an air pump, pressure and flow sensors, flexible (non-kinking) tubing, and connectors to specifically to couple to an endoscope, among other components.

The flush control equipment integrated within the testing and cleaning unit 500 may be controlled with use of the control unit. The flush control equipment may perform a chemical flushing of the internal lumen of the subject endoscope using a chemical fluid, perform one or more measurement of flushed fluids, and output a result of the chemical flushing on the display screen 504. The flush control equipment may include a fluid pump, pressure/flow sensors, delivery tubing, port connections, and filters, among other components. Further, the flush control equipment may be configured to perform a rinsing procedure, before, after, or during a fluid cleaning flush.

The testing and cleaning unit 500 is also shown as integrating with two sets of optical inspection equipment. The first set of optical inspection equipment is an illustrated borescope unit 530 that includes: a probe 534 (e.g., a flexible elongate member) having a digital imaging sensor (e.g., disposed at a distal end), with the probe shaped and sized to pass through the internal lumen of the subject endoscope; a imaging unit 532 coupled to a proximate end of the probe 534, with the imaging unit configured to provide light into the internal lumen via the flexible elongate member and receive the digital imaging of the internal lumen from the digital imaging sensor; and an electrical connection 514 which electrically couples to the testing and cleaning unit 500 (with coupling not shown). The imaging data that is captured by the digital imaging sensor may be viewed, captured, processed, and/or displayed by the unit 500, including via real-time or playback on the display screen 504. The borescope unit 530 is hosted externally to the housing 502; FIG. 5 illustrates the attachment of the borescope unit 530 to the side of the housing 502 with a bracket 518B.

The second set of optical inspection equipment integrating with the testing and cleaning unit 500 is a magnification imaging device 520 that includes: a housing 522 defining a handle portion 526 and display portion, a display screen 524 exposed from the housing 522 to provide a magnification image output, and control buttons 528 to allow display and control of the magnification. On the opposite side of the display screen 524, a camera (e.g., digital image sensor, and in some examples, light source) is exposed to capture the digital image data. The magnification imaging device 520 is also hosted externally to the housing 502; FIG. 5 illustrates a bracket 518A allowing the attachment of this unit on another side of the housing 502 (a side opposite of the bracket 518B). The magnification imaging device 520 also depicts a magnified image being output on the display screen 524, with a magnified closeup of an area 542 of an endoscope insertion tube 540.

The output from either of the optical inspection equipment 520, 530 may be provided on the display screen 504 (not illustrated), in real time, or in an image review mode. Additionally, either of the optical inspection equipment 520 or the testing and cleaning unit 500 may include access ports (e.g., USB ports, SD card ports) or communication circuitry (e.g., for network communication) that enables the transfer of data from the testing and cleaning unit 500 or optical inspection equipment 520, 530. Thus, either of the optical inspection equipment 520, 530 may include processing circuitry and logic to for operational control, capture, and transmission of imaging data.

Figure 6:
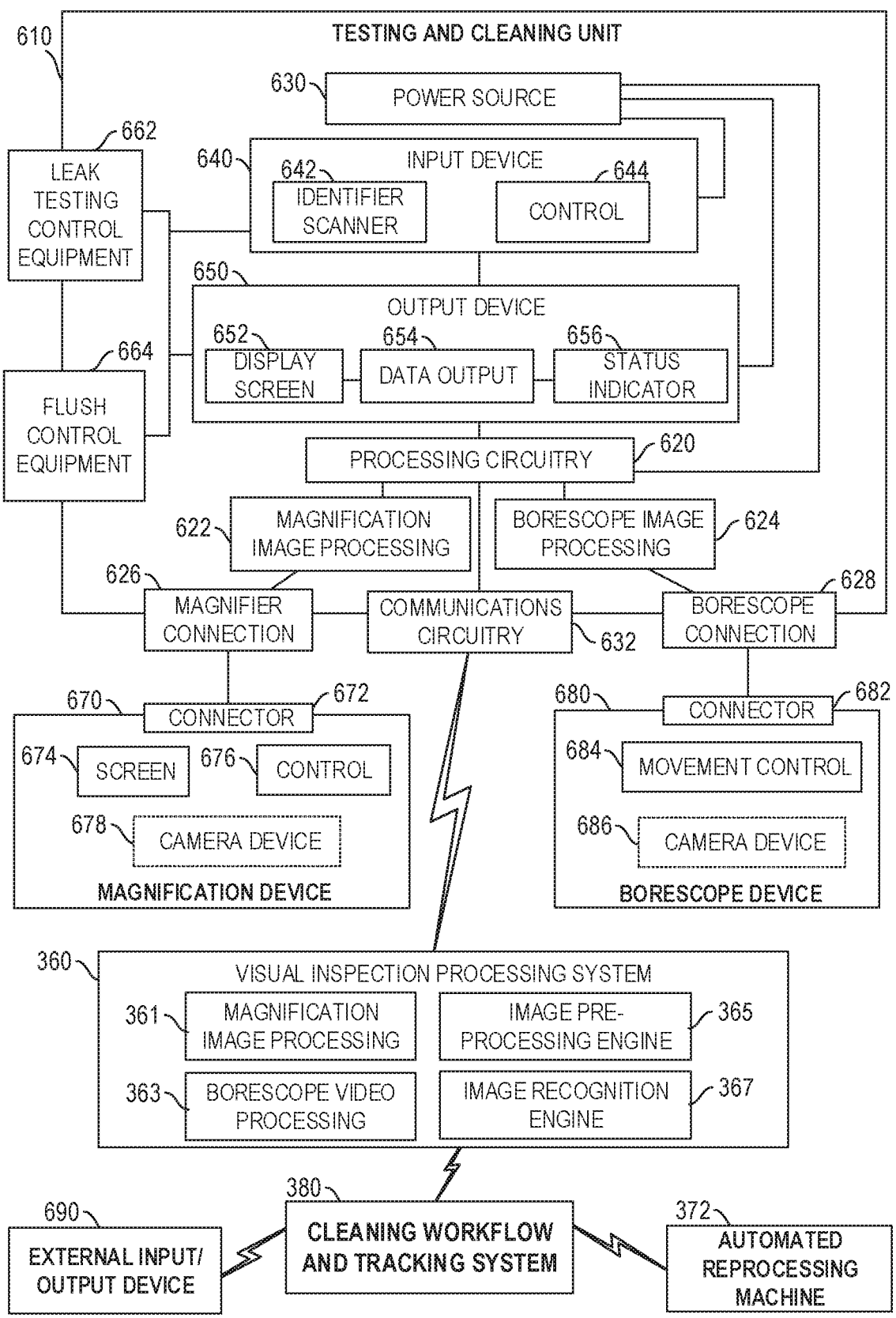
FIG. 6 is a block diagram that illustrates components and functionality of a cleaning and inspection system, according to various examples discussed herein.

FIG. 6 is a block diagram that illustrates components and functionality of the endoscope cleaning and inspection system. Specifically, the testing and cleaning unit 610 is shown as including (e.g., hosting, coupling to, controlling) processing circuitry 620, a power source 630, input device 640, and an output device 650. The testing and cleaning unit 610 is shown as operably connected to a magnification device 670 via a magnifier electrical connection 626, and operably connected to a borescope device 680 via a borescope electrical connection 628. Further, the testing and cleaning unit 610 is shown as operably connected to the visual inspection processing system 360 via communications circuitry 632, which may embody aspects of wireless or wired communications and protocols.

In an example, the input device 640 may include an identifier scanner 642 (e.g., a barcode reader or RFID interrogator) adapted to capture an identifier of a subject endoscope (e.g., from a barcode or RFID tag) or an identifier of an operator (e.g., a barcode or RFID tag, such as provided in an employee badge); and control 644 (e.g., button, electromechanical actuator) adapted to control or affect the operation of the leak testing control equipment 662, flush control equipment 664, optical inspection equipment (e.g., 670, 680), or operational aspects of the testing and cleaning unit 610. In an example, the output device 650 may include a display screen 652 (e.g., a LCD screen/touch screen) adapted to provide a results of leak test, chemical flushing, and/or optical inspection operations; a data output component 654 (e.g., a data output port, such as a USB or serial port) adapted to provide data from the results of the leak test, chemical flushing, and/or optical inspection operations, and internal operations of the testing and cleaning unit 610; and a status indicator 656 (e.g., a electromechanical gauge, LED light, LED character display, etc.) adapted to indicate a status of the respective leak test, chemical flushing, and/or optical inspection operations. Other types of human input devices, output mechanisms, and electronic controls may also be incorporated.

The input device 640 and output device 650 is shown as being coupled to processing circuitry 620, leak testing control equipment 662, and flush control equipment 664. In an example, the processing circuitry 620 operates a magnification image processing component 622 (e.g., logic implemented in hardware) for digital processing and enhancement (e.g., enlargement, selection) of image data captured by the magnification device 670, and a borescope image processing component 624 (e.g., logic implemented in hardware) for digital processing and enhancement of image data captured by the borescope device 680. Images that result from either image processing component 622, 624 may be output via the display screen 652 or exported via the data output component 654.

In an example, the leak testing control equipment 662 enables electromechanical control and monitoring of pumps and fluid (e.g., air, liquid, and pressure) control components used to perform leak testing of a connected endoscope. The leak testing control equipment 662 is further controllable by input device 640 (e.g., via control 644) and provides an indication of a status of the leak testing procedure and results to the output device 650 (e.g., via the status indicator 656). Likewise, the flush control equipment 664 enables electromechanical control and monitoring of pumps and fluid (e.g., air, liquid, including water and detergent) to perform a chemical flush of the connected endoscope, and is also controllable by input device 640 (e.g., via control 644) and provides an indication of a status of the flushing procedure and results to the output device 650 (e.g., via the status indicator 656).

The magnification device 670, which in some examples is a component of the testing and inspection system, may include a connector 672 to electrically couple (e.g., with a power or data connection) to the unit 610 via the magnifier electrical connection 626. The magnification device 670 may include a screen 674, one or more controls 676, and a camera device 678 (e.g., a CCD/CMOS sensor, optical lens, etc.). In other examples, the camera device 678 is operably connected to but not directly housed within the magnification device. The camera device 678 may also be operable with the use of a light source for illumination.

The borescope device 680, which in some examples is a component of the testing and inspection system, may include a connector 682 to electrically couple (e.g., with a power or data connection) to the unit 610 via the borescope electrical connection 628. The borescope device 680 may include a movement control 684 which provides a steady mechanical advancement within a lumen at a consistent rate. The borescope device 680 may also include a camera device 678 (e.g., a CCD/CMOS sensor, optical lens, etc.) disposed at the probe end (e.g., at the distal tip) or at the optical control unit end (e.g., at the proximal end, connected to the distal tip via a light pipe) of the borescope device 680.

In the depiction of FIG. 6, the visual inspection processing system 360 includes components which are adapted for processing of imaging data from the magnification device 670 and/or the borescope device 680. These components may include, a magnification image processing 361 (e.g., implemented in logic, configured circuitry, etc.) to extract or capture images from the magnification device 670; borescope video processing 363 (e.g., implemented in logic, configured circuitry, etc.) to extract or capture images from the borescope device 680; an image pre-processing engine 365 to perform pre-processing (e.g., cropping, resizing, enhancement) from the extracted or captured images; and an image recognition engine 367 to implement a model (e.g., machine learning model, or other trained classifier) to classify, analyze, or determine values from the extracted or captured images.

The visual inspection processing system 360 may also communicate results of image recognition, statuses, or image data, directly to the cleaning workflow and tracking system 380. In other examples, the testing and cleaning unit 610 may also directly communicate with the cleaning workflow and tracking system 380 (e.g., via communications circuitry 632). Additionally, in some examples, the cleaning workflow and tracking system 380 may integrate with one or more external input/output devices 690 to provide human input/output in connection with the testing and cleaning operations or visual inspection operations; the cleaning workflow and tracking system 380 may also provide information and data to one or more automated reprocessing machines 372, such as in connection with test results, flushing procedure results, and the like.

Figure 7:
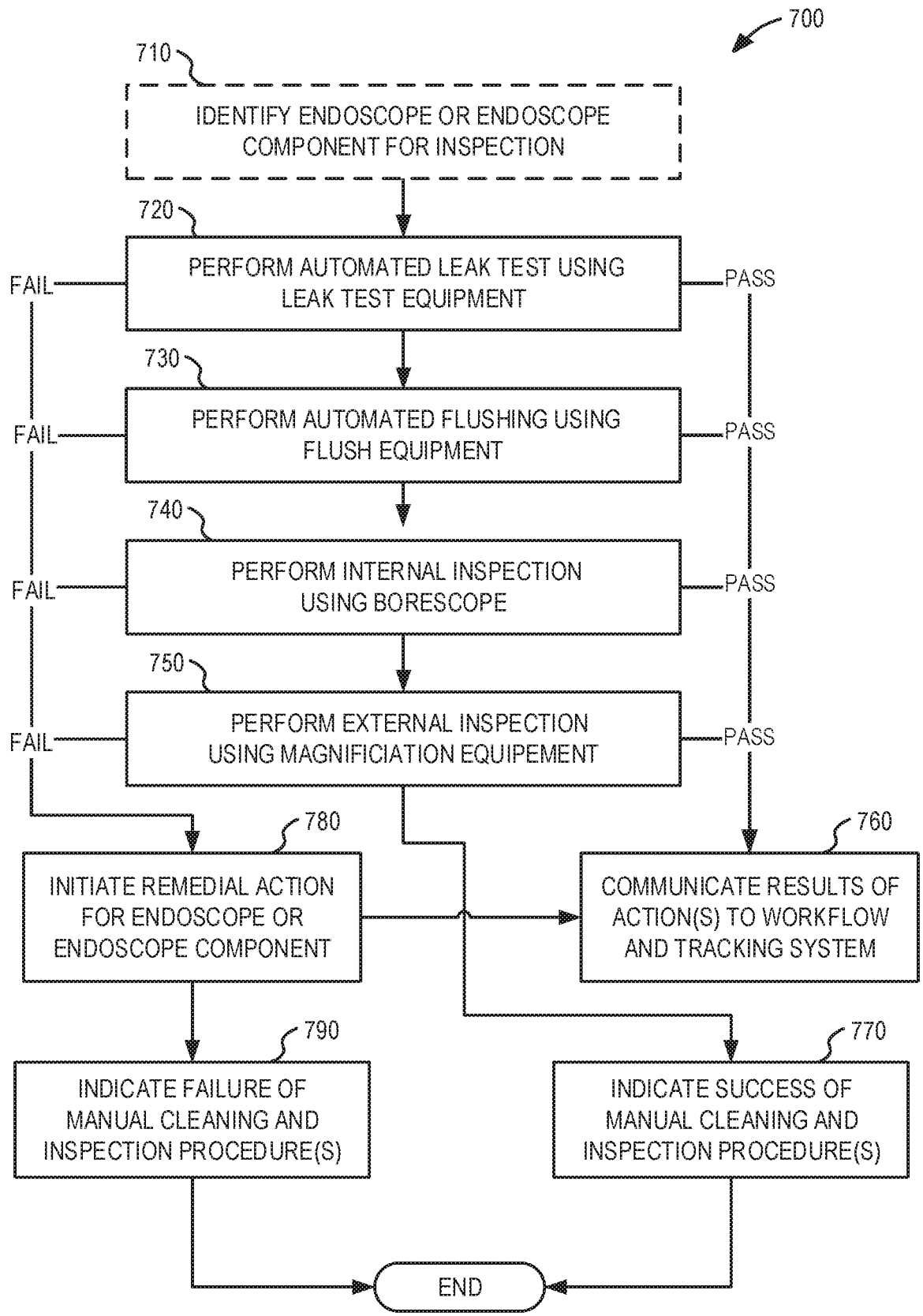
FIG. 7 illustrates a flowchart for a method of endoscope testing and inspection, according to various examples discussed herein.

FIG. 7 illustrates a flowchart 700 for a method of endoscope testing and inspection, using a testing and cleaning unit (e.g., the unit 128, 500, 610, as discussed above). The flowchart commences at 710 with the optional identifying of the endoscope or endoscope component for inspection. In an example, this includes capturing an identifier of the subject endoscope, using an input device operably coupled to the testing and cleaning unit. For instance, the input device may include a barcode scanner or an RFID scanner, to obtain an identifier included in a barcode or RFID tag on the subject endoscope.

The flowchart 700 continues at 720 with the performance of a leak test of an internal lumen of the subject endoscope using pressure via the fluid connection, and at 730 with the performance of a chemical flush of the internal lumen of the subject endoscope using a chemical fluid via the fluid connection. In an example, the leak test and the chemical flush is performed based on a fluid connection that is established between one or more ports of the subject endoscope and one or more fluid connectors of the testing and cleaning unit. The respective results of the leak test and the chemical flush may be indicated or otherwise output on a display screen of the testing and cleaning unit, the leak test or chemical flushing equipment, or other system components.

In an example, if the leak test or flushing procedure fails, a remedial action at 780 for the endoscope or endoscope component may be initiated (e.g., with the testing and cleaning unit, the cleaning workflow and tracking system, or with other manual processes); additionally, the failure of the manual cleaning and inspection procedures may also be indicated at 790 (e.g., with the testing and cleaning unit, the cleaning workflow and tracking system, or with manual actions).

Any remedial action and the result of any remedial action may be communicated at 760 to the cleaning workflow and tracking system. Additionally, in an example, if the leak test or flushing procedure completes successfully (a pass), then the results of the action may be communicated at 760 to the cleaning workflow and tracking system. Either results or actions may be tracked by the cleaning workflow and tracking system based on the identifier obtained for the subject endoscope.

The flowchart 700 continues by performing, with optical inspection equipment operably coupled to the testing and cleaning unit, digital imaging of an inspected area of the subject endoscope. In an example, illustrated at 740, this optical inspection may include performing an internal inspection of one or more lumen of the endoscope using a borescope imaging device external to the testing and cleaning unit. Also in an example, illustrated at 750, this optical inspection may include performing an external inspection using a magnification imaging device external to the testing and cleaning unit.

In a further example, the internal inspection involves moving (e.g., advancing, retracting) the borescope imaging device through the internal lumen of the subject endoscope, and outputting digital imaging on the display screen to output a plurality of images or video obtained with the borescope imaging device.

Also in a further example, the external inspection involves receiving a data stream from the magnification imaging device that is moved (e.g., with an automated device, or with human movement) above an external surface area of the subject endoscope to obtain a magnification of the external surface area, and outputting digital imaging on the display screen to output a plurality of images or video from the data stream obtained with the magnification imaging device. In some examples, the magnification image or video is output on a monitoring display screen of the magnification imaging device concurrently (at the same time) as being shown on the display screen of the testing and cleaning unit.

Similar to the results of a leak testing or flushing procedure failure discussed above, any failure to perform internal inspection, the identification of defects, or the identification of a compromised state of the endoscope, may be followed by initiation of a remedial action for the endoscope or any affected component(s) at 780. Such failure of the manual cleaning and/or the inspection procedure may be indicated, such as with an output on the testing and cleaning unit, at 790, or with an output directly on the magnification imaging device or borescope imaging device.

Likewise, similar to the result of a leak testing or flushing procedure discussed above, the success may be communicated to the cleaning workflow and tracking system at 760, and indicated at 770. Other variations and uses of the cleaning workflow and tracking system, and devices connected to the workflow and tracking system, may also be used.

Although many of the preceding examples were provided with reference to endoscope processing and similar medical device cleaning settings, it will be understood that a variety of other uses may be applied in both medical and non-medical settings to identify, prevent, or reduce the potential of contamination. These settings may include the handling of hazardous materials in a various of scientific and industrial settings, such as the handling of objects contaminated with biological or radioactive agents; the human control of systems and devices configured to process and clean potentially contaminated objects; and other settings involving a contaminated object or human. Likewise, the preceding examples may also be applicable in clean room settings where the environment or particular objects are intended to remain in a clean state, and where human contact with substances or objects may cause contamination that is tracked and remediated.

FIG. 8 is a block diagram illustrating an example computer system machine upon which any one or more of the previous techniques may be performed or facilitated by. Computer system 800 specifically may be used in connection with facilitating the operations of the cleaning workflow and tracking system 380, the visual inspection processing system 360, the user computing system 430, or any other computing platform described or referred to herein. In alternative embodiments, the machine operates as a standalone device or may be connected (e.g., networked) to other machines. In a networked deployment, the machine may operate in the capacity of either a server or a client machine in server-client network environments, or it may act as a peer machine in peer-to-peer (or distributed) network environments. The machine may be a personal computer (PC), a tablet PC, a smartphone, a web appliance, or any machine capable of executing instructions (sequential or otherwise) that specify actions to be taken by that machine. Further, while only a single machine is illustrated, the term "machine" shall also be taken to include any collection of machines that individually or jointly execute a set (or multiple sets) of instructions to perform any one or more of the methodologies discussed herein.

Example computer system 800 includes a processor 802 (e.g., a central processing unit (CPU), a graphics processing unit (GPU) or both), a main memory 804 and a static memory 806, which communicate with each other via a link 808 (e.g., an interlink, bus, etc.). The computer system 800 may further include a video display unit 810, an alphanumeric input device 812 (e.g., a keyboard), and a user interface (UI) navigation device 814 (e.g., a mouse). In an example, the video display unit 810, input device 812 and UI navigation device 814 are a touch screen display. The computer system 800 may additionally include a storage device 816 (e.g., a drive unit), a signal generation device 818 (e.g., a speaker), and a network interface device 820 which may operably communicate with a communications network 826 using wired or wireless communications hardware. The computer system 800 may further include one or more human input sensors 828 configured to obtain input (including non-contact human input) in accordance with input recognition and detection techniques. The human input sensors 828 may include a camera, microphone, barcode reader, RFID reader, near field communications reader, or other sensor producing data for purposes of input. The computer system 800 may further include an output controller 830, such as a serial (e.g., universal serial bus (USB), parallel, or other wired or wireless (e.g., infrared (IR)) connection to communicate or control one or more peripheral devices (e.g., a printer, card reader, etc.).

The storage device 816 may include a machine-readable medium 822 on which is stored one or more sets of data structures or instructions 824 (e.g., software) embodying or utilized by any one or more of the methodologies or functions described herein. The instructions 824 may also reside, completely or at least partially, within the main memory 804, static memory 806, and/or within the processor 802 during execution thereof by the computer system 800, with the main memory 804, static memory 806, and the processor 802 also constituting machine-readable media.

While the machine-readable medium 822 is illustrated in an example embodiment to be a single medium, the term "machine-readable medium" may include a single medium or multiple media (e.g., a centralized or distributed database, and/or associated caches and servers) that store the one or more instructions 824. The term "machine-readable medium" shall also be taken to include any tangible medium (e.g., a non-transitory medium) that is capable of storing, encoding or carrying instructions for execution by the computer system 800 and that cause the computer system 800 to perform any one or more of the methodologies of the present disclosure or that is capable of storing, encoding or carrying data structures utilized by or associated with such instructions. The term "machine-readable medium" shall accordingly be taken to include, but not be limited to, solid-state memories, and optical and magnetic media. Specific examples of machine-readable media include non-volatile memory, including, by way of example, semiconductor memory devices (e.g., Electrically Programmable Read-Only Memory (EPROM), Electrically Erasable Programmable Read-Only Memory (EEPROM)) and flash memory devices; magnetic disks such as internal hard disks and removable disks; magneto-optical disks; and CD-ROM and DVD-ROM disks.

The instructions 824 may further be transmitted or received over a communications network 826 using a transmission medium via the network interface device 820 utilizing any one of a number of well-known transfer protocols (e.g., frame relay, internet protocol (IP), transmission control protocol (TCP), user datagram protocol (UDP), hypertext transfer protocol (HTTP)). Examples of communication networks include a local area network (LAN), wide area network (WAN), the Internet, mobile telephone networks, Plain Old Telephone (POTS) networks, and wireless data networks (e.g., Wi-Fi, 3G, and 4G LTE/LTE-A or 5G networks). The term "transmission medium" shall be taken to include any intangible medium that is capable of storing, encoding, or carrying instructions for execution by the computing system 800, and includes digital or analog communications signals or other intangible medium to facilitate communication of such software.

As an additional example, computing embodiments described herein may be implemented in one or a combination of hardware, firmware, and software. Embodiments may also be implemented as instructions stored on a computer-readable storage device, which may be read and executed by at least one processor to perform the operations described herein. A computer-readable storage device may include any non-transitory mechanism for storing information in a form readable by a machine (e.g., a computer). For example, a computer-readable storage device may include read-only memory (ROM), random-access memory (RAM), magnetic disk storage media, optical storage media, flash-memory devices, and other storage devices and media.

It should be understood that the functional units or capabilities described in this specification may have been referred to or labeled as components or modules, in order to more particularly emphasize their implementation independence. Component or modules may be implemented in any combination of hardware circuits, programmable hardware devices, other discrete components. Components or modules may also be implemented in software for execution by various types of processors. An identified component or module of executable code may, for instance, comprise one or more physical or logical blocks of computer instructions, which may, for instance, be organized as an object, procedure, or function. Nevertheless, the executables of an identified component or module need not be physically located together, but may comprise disparate instructions stored in different locations which, when joined logically together, comprise the component or module and achieve the stated purpose for the component or module. Indeed, a component or module of executable code may be a single instruction, or many instructions, and may even be distributed over several different code segments, among different programs, and across several memory devices.

Similarly, operational data may be identified and illustrated herein within components or modules, and may be embodied in any suitable form and organized within any suitable type of data structure. The operational data may be collected as a single data set, or may be distributed over different locations including over different storage devices, and may exist, at least partially, merely as electronic signals on a system or network. The components or modules may be passive or active, including agents operable to perform desired functions.

Additional examples of the presently described method, system, and device embodiments include the following, non-limiting configurations. Each of the following non-limiting examples may stand on its own, or may be combined in any permutation or combination with any one or more of the other examples provided below or throughout the present disclosure.

Example 1 is an endoscope cleaning and inspection system, comprising: an endoscope testing and cleaning unit, adapted to couple to a subject endoscope, the testing and cleaning unit including: a display screen; a control unit; and a fluid connector arranged to removably couple with a port of the subject endoscope via a tube, to access an internal lumen within the subject endoscope; leak testing equipment comprising a pump and pressure sensor configured to, under control of the control unit, perform a leak test of the internal lumen of the subject endoscope using fluid pressure; flush control equipment comprising a pump, pressure sensor, and detergent container, the equipment configured to, under control of the control unit, perform a chemical flushing of the internal lumen of the subject endoscope using a chemical fluid; and optical inspection equipment comprising an imaging element operably coupled to the testing and cleaning unit, the equipment configured to capture digital imaging of an inspected area of the subject endoscope; wherein the endoscope testing and cleaning unit is adapted to receive and output a result of the leak test, a result of the chemical flushing, and a result of the digital imaging on the display screen.

In Example 2, the subject matter of Example 1 includes, subject matter where the optical inspection equipment comprises a borescope imaging device external to the testing and cleaning unit, the borescope imaging device including: a flexible elongate member including a digital imaging sensor, the flexible elongate member shaped and sized to pass through the internal lumen of the subject endoscope; and an imaging unit coupled to a proximate end of the flexible elongate member, the imaging unit configured to provide light into the internal lumen via the flexible elongate member and receive the digital imaging of the internal lumen from the digital imaging sensor.

In Example 3, the subject matter of Example 2 includes, subject matter where the testing and cleaning unit further comprises an electrical connection port to operably couple to the borescope imaging device, to receive the digital imaging via an electrical connection port of the borescope imaging device.

In Example 4, the subject matter of Examples 2-3 includes, subject matter where the borescope imaging device further comprises a control button, the control button operable to control a capture of the digital imaging from the digital imaging sensor.

In Example 5, the subject matter of Examples 1-4 includes, subject matter where the optical inspection equipment comprises a magnification imaging device external to the testing and cleaning unit, the magnification imaging device including: a housing including a handle; a digital imaging sensor disposed on a first side of the housing and configured to capture the digital imaging; and imaging control circuitry configured to capture the digital imaging of a surface of the subject endoscope and provide magnification of the digital imaging to the testing and cleaning unit.

In Example 6, the subject matter of Example 5 includes, subject matter where the magnification imaging device further comprises a monitoring display screen exposed from a portion of the housing of the magnification imaging device, wherein the imaging control circuitry is adapted to output a representation of the magnification of the digital imaging on the monitoring display screen.

In Example 7, the subject matter of Examples 5-6 includes, subject matter where the magnification imaging device further comprises a control button exposed from a portion of the housing of the magnification imaging device, the control button operable to control a capture of the digital imaging and control the magnification of the digital imaging.

In Example 8, the subject matter of Examples 5-7 includes, subject matter where the magnification imaging device further comprises a lighting device exposed from a portion of the housing of the magnification imaging device, the lighting device located adjacent to the digital imaging sensor, and wherein the lighting device is controllable to illuminate an area captured with the digital imaging.

In Example 9, the subject matter of Examples 5-8 includes, subject matter where the testing and cleaning unit further comprises an electrical connection port to operably couple to the magnification imaging device, to receive the digital imaging via an electrical connection port of the magnification imaging device.

In Example 10, the subject matter of Examples 1-9 includes, subject matter where the display screen of the testing and cleaning unit is a touch screen, wherein the touch screen is configured to receive user input to control the leak test, chemical flushing, and output of the digital imaging.

In Example 11, the subject matter of Examples 1-10 includes, subject matter where the control unit is coupled to a user input device to change an operation state of the leak test, the chemical flushing, or output of the digital imaging, using the respective equipment.

In Example 12, the subject matter of Examples 1-11 includes, subject matter where the control unit includes detection circuitry to perform automatic control of the leak test, the chemical flushing, and the digital imaging, using the respective equipment.

In Example 13, the subject matter of Examples 1-12 includes, subject matter where the display screen, the leak testing equipment, and the flush control equipment are hosted within a common housing of the testing and cleaning unit, and wherein the display screen is exposed at least in part from the common housing.

In Example 14, the subject matter of Examples 1-13 includes, an input device to capture an identifier of the subject endoscope.

In Example 15, the subject matter of Example 14 includes, subject matter where the input device comprises a barcode scanner or an RFID scanner, to obtain an identifier included in a barcode or RFID tag on the subject endoscope.

In Example 16, the subject matter of Examples 14-15 includes, communication circuitry to communicate the result of the leak test and the result of the chemical flushing for the subject endoscope to a tracking system, to track the results based on the identifier of the subject endoscope.

In Example 17, the subject matter of Examples 1-16 includes, processing circuitry to execute logic for control and monitoring of the leak test, the chemical flushing, and the digital imaging, in respective stages; wherein the processing circuitry is adapted to provide output, to the display screen, of a status of the monitoring of the leak test, the chemical flushing, and the digital imaging, in the respective stages.

Example 18 is an endoscope testing and cleaning unit, comprising: a housing; a connection port provided from the housing, adapted to establish a fluid channel with an internal lumen of a subject endoscope; leak testing equipment hosted within the housing, the leak testing equipment configured to perform a leak test of the internal lumen of the subject endoscope using fluid pressure; flush control equipment hosted within the housing, the flush control equipment configured to perform a chemical flushing of the internal lumen of the subject endoscope using a chemical fluid; a first imaging connection port to connect to a borescope imaging device, the borescope imaging device providing digital imaging of the internal lumen of the subject endoscope; a second imaging connection port to connect to a magnifier imaging device, the magnifier imaging device providing digital imaging of an area of an external surface of the subject endoscope; and a display screen adapted to output a result of the digital imaging on the display screen.

In Example 19, the subject matter of Example 18 includes, subject matter where the display screen is further adapted to output a result of the leak test and the chemical flushing on the display screen.

In Example 20, the subject matter of Examples 18-19 includes, subject matter where the display screen of the testing and cleaning unit is a touch screen, wherein the touch screen is configured to receive user control to control the leak test, chemical flushing, and the digital imaging.

In Example 21, the subject matter of Examples 18-20 includes, a control unit adapted to perform and monitor the leak test and the chemical flushing.

In Example 22, the subject matter of Examples 18-21 includes, a user input device to provide a user control of the leak test, the chemical flushing, and an output of the digital imaging, with the respective equipment.

In Example 23, the subject matter of Examples 18-22 includes, processing circuitry to execute logic for control and monitoring of the leak test, the chemical flushing, and the digital imaging, in respective stages; wherein the display screen is adapted to output a status of the monitoring of the leak test, the chemical flushing, and the digital imaging, in the respective stages.

In Example 24, the subject matter of Example 23 includes, the processing circuitry to further execute logic for a capture of digital imaging.

In Example 25, the subject matter of Examples 23-24 includes, an input device used to trigger a capture of an image from the digital imaging.

In Example 26, the subject matter of Examples 18-25 includes, an input device to obtain an identifier of the subject endoscope.

In Example 27, the subject matter of Example 26 includes, communication circuitry to communicate the result of the leak test and the result of the chemical flushing for the subject endoscope to a tracking system, based on the identifier of the subject endoscope.

In Example 28, the subject matter of Examples 18-27 includes, the housing further comprising: a first attachment bracket, coupled to the housing, shaped to host the borescope imaging device, wherein the first attachment bracket allows removeable storage of the borescope imaging device; and a second attachment bracket, coupled to the housing, shaped to host the magnifier imaging device, wherein the first attachment bracket allows removeable storage of the magnification imaging device.

In Example 29, the subject matter of Examples 18-28 includes, the housing further comprising: a third attachment bracket, coupled to the housing, shaped to host a leak test connector, wherein the third attachment bracket allows removeable storage of the leak test connector.

In Example 30, the subject matter of Examples 18-29 includes, subject matter where the first and second imaging connection ports respectively include a power channel and communication channel, to provide power and obtain digital imaging data from the respective devices.

In Example 31, the subject matter of Examples 18-30 includes, subject matter where the connection port comprises first connection ports used to perform leak testing, and a second connection ports used to perform chemical flushing.

In Example 32, the subject matter of Examples 18-31 includes, subject matter where the connection port is coupled to the internal lumen of the subject endoscope, via the fluid channel, as established with a tube removably coupled between the connection port and an access port of the subject endoscope.

Example 33 is a method of testing and cleaning of a subject endoscope, performed with an endoscope testing and cleaning unit, comprising: establishing a fluid connection between a port of the subject endoscope and a fluid connector of the testing and cleaning unit; performing, with the testing and cleaning unit, a leak test of an internal lumen of the subject endoscope using pressure via the fluid connection; performing, with the testing and cleaning unit, a chemical flush of the internal lumen of the subject endoscope using a chemical fluid via the fluid connection; outputting respective results of the leak test and the chemical flush on a display screen of the testing and cleaning unit; performing, with optical inspection equipment operably coupled to the testing and cleaning unit, digital imaging of an inspected area of the subject endoscope; and outputting a result of the digital imaging on the display screen of the testing and cleaning unit.

In Example 34, the subject matter of Example 33 includes, subject matter where the optical inspection equipment comprises a borescope imaging device external to the testing and cleaning unit, wherein the method further comprises: moving the borescope imaging device through the internal lumen of the subject endoscope, wherein the digital imaging that is output on the display screen comprises a plurality of images or video obtained with the borescope imaging device.

In Example 35, the subject matter of Example 34 includes, subject matter where performing the digital imaging comprises receiving the digital imaging via an electrical connection established between the testing and cleaning unit and the borescope imaging device.

In Example 36, the subject matter of Examples 33-35 includes, subject matter where the optical inspection equipment comprises a magnification imaging device external to the testing and cleaning unit, wherein the method further comprises: receiving a data stream from the magnification imaging device being moved above an external surface area of the subject endoscope, to obtain a magnification of the external surface area, wherein the digital imaging that is output on the display screen comprises a plurality of images or video from the data stream obtained with the magnification imaging device.

In Example 37, the subject matter of Example 36 includes, outputting a representation of the magnification on a monitoring display screen of the magnification imaging device concurrently with outputting the magnification on the display screen of the testing and cleaning unit.

In Example 38, the subject matter of Examples 33-37 includes, receiving the digital imaging via an electrical connection established between the testing and cleaning unit and the optical inspection equipment.

In Example 39, the subject matter of Example 38 includes, providing power from the testing and cleaning unit to the optical inspection equipment, via the electrical connection.

In Example 40, the subject matter of Examples 33-39 includes, subject matter where the display screen of the testing and cleaning unit is a touch screen, and wherein the method further comprises: receiving user input via the touch screen to control the leak test, the chemical flush, and output of the digital imaging.

In Example 41, the subject matter of Examples 33-40 includes, changing an operation state of the leak test, the chemical flush, or output of the digital imaging, using the respective equipment, based on input received from a user input device of the testing and cleaning unit.

In Example 42, the subject matter of Examples 33-41 includes, subject matter where the display screen, leak testing equipment, and fluid control equipment are hosted within a common housing of the testing and cleaning unit, and wherein the display screen is exposed at least in part from the common housing.

In Example 43, the subject matter of Examples 33-42 includes, capturing an identifier of the subject endoscope, using an input device operably coupled to the testing and cleaning unit.

In Example 44, the subject matter of Example 43 includes, subject matter where the input device comprises a barcode scanner or an RFID scanner, and wherein the method further comprises: using the barcode scanner or the RFID scanner, to obtain an identifier included in a barcode or RFID tag on the subject endoscope.

In Example 45, the subject matter of Examples 43-44 includes, communicating the result of the leak test and the result of the chemical flush for the subject endoscope to a tracking system, to track the results based on the identifier of the subject endoscope.

In Example 46, the subject matter of Examples 33-45 includes, outputting a respective status of the leak test, the chemical flush, and the digital imaging, in respective stages of that perform the leak test, the chemical flushing, and the digital imaging.

The following claims are hereby incorporated into the detailed description, with each claim standing on its own as a separate embodiment.

What is claimed is:
1. An endoscope testing and cleaning unit, comprising:
a housing;
a connection port provided from the housing, adapted to establish a fluid channel with an internal lumen of a subject endoscope;
leak testing equipment hosted within the housing, the leak testing equipment configured to perform a leak test of the internal lumen of the subject endoscope using fluid pressure;
flush control equipment hosted within the housing, the flush control equipment configured to perform a chemical flushing of the internal lumen of the subject endoscope using a chemical fluid;
a first imaging connection port to connect to a borescope imaging device, the borescope imaging device providing digital imaging of the internal lumen of the subject endoscope;
a second imaging connection port to connect to a magnifier imaging device, the magnifier imaging device providing digital imaging of an area of an external surface of the subject endoscope; and a display screen adapted to output a result of the digital imaging on the display screen.

2. The endoscope testing and cleaning unit of claim 1, wherein the display screen is further adapted to output a result of the leak test and the chemical flushing on the display screen.

3. The endoscope testing and cleaning unit of claim 1, wherein the display screen of the testing and cleaning unit is a touch screen, wherein the touch screen is configured to receive user control to control the leak test, chemical flushing, and the digital imaging.

4. The endoscope testing and cleaning unit of claim 1, further comprising:
a control unit adapted to perform and monitor the leak test and the chemical flushing.

5. The endoscope testing and cleaning unit of claim 1, further comprising:
a user input device to provide a user control of the leak test, the chemical flushing, and an output of the digital imaging, with the respective equipment.

6. The endoscope testing and cleaning unit of claim 1, further comprising:
processing circuitry to execute logic for control and monitoring of the leak test, the chemical flushing, and the digital imaging, in respective stages;
wherein the display screen is adapted to output a status of the monitoring of the leak test, the chemical flushing, and the digital imaging, in the respective stages.

7. The endoscope testing and cleaning unit of claim 6, wherein the processing circuitry is to further execute logic for a capture of digital imaging.

8. The endoscope testing and cleaning unit of claim 6, further comprising:
an input device used to trigger a capture of an image from the digital imaging.

9. The endoscope testing and cleaning unit of claim 1, further comprising:
an input device to obtain an identifier of the subject endoscope.

10. The endoscope testing and cleaning unit of claim 9, further comprising:
communication circuitry to communicate the result of the leak test and the result of the chemical flushing for the subject endoscope to a tracking system, based on the identifier of the subject endoscope.

11. The endoscope testing and cleaning unit of claim 1, the housing further comprising:
a first attachment bracket, coupled to the housing, shaped to host the borescope imaging device, wherein the first attachment bracket allows removeable storage of the borescope imaging device; and
a second attachment bracket, coupled to the housing, shaped to host the magnifier imaging device, wherein the first attachment bracket allows removeable storage of the magnification imaging device.

12. The endoscope testing and cleaning unit of claim 1, the housing further comprising:
a third attachment bracket, coupled to the housing, shaped to host a leak test connector, wherein the third attachment bracket allows removeable storage of the leak test connector.

13. The endoscope testing and cleaning unit of claim 1, wherein the first and second imaging connection ports respectively include a power channel and communication channel, to provide power and obtain digital imaging data from the respective devices.

14. The endoscope testing and cleaning unit of claim 1, wherein the connection port comprises first connection ports used to perform leak testing, and a second connection ports used to perform chemical flushing.

15. The endoscope testing and cleaning unit of claim 1, wherein the connection port is coupled to the internal lumen of the subject endoscope, via the fluid channel, as established with a tube removably coupled between
the connection port and an access port of the subject endoscope.

* * * * *